(12) United States Patent
Davis

(10) Patent No.: US 8,905,543 B2
(45) Date of Patent: Dec. 9, 2014

(54) SLIT LAMP ADAPTOR FOR PORTABLE CAMERA

(76) Inventor: Andrew Peter Davis, Bellevue, WA (US)

( * ) Notice: Subject to any disclaimer, the term of this patent is extended or adjusted under 35 U.S.C. 154(b) by 116 days.

(21) Appl. No.: 13/467,916

(22) Filed: May 9, 2012

(65) Prior Publication Data

US 2012/0287402 A1    Nov. 15, 2012

Related U.S. Application Data

(60) Provisional application No. 61/518,610, filed on May 9, 2011.

(51) Int. Cl.
*A61B 3/14* (2006.01)
*G03B 17/56* (2006.01)

(52) U.S. Cl.
CPC .............. *A61B 3/14* (2013.01); *G03B 17/568* (2013.01)
USPC ........................................ 351/206; 351/205

(58) Field of Classification Search
USPC .................................................. 351/200–247
See application file for complete search history.

(56) References Cited

U.S. PATENT DOCUMENTS

| 5,293,532 | A  | * | 3/1994  | Marshall ..................... 351/225 |
| 6,674,476 | B1 | * | 1/2004  | Suzuki ......................... 348/375 |
| 2005/0270484 | A1 | * | 12/2005 | Maeda et al. ................ 351/206 |
| 2011/0063620 | A1 | * | 3/2011  | Wojtkowski et al. ........ 356/479 |
| 2011/0085138 | A1 | * | 4/2011  | Filar ............................. 351/206 |

* cited by examiner

*Primary Examiner* — William Choi
*Assistant Examiner* — Sharrief Broome
(74) *Attorney, Agent, or Firm* — Lowe Graham Jones, PLLC

(57) ABSTRACT

An adaptor for a slit lamp holds a portable camera, such as a cell phone, in place relative to a slit lamp. The adaptor is adjustable to accommodate virtually any size of portable camera through the use of screws, washers, spacers, and other adjustment mechanisms. The adaptor can be formed in two parts: an ocular engaging portion and a camera support. The two portions can be coupled together to position the camera relative to the slit lamp to photograph a patient's eye.

21 Claims, 4 Drawing Sheets

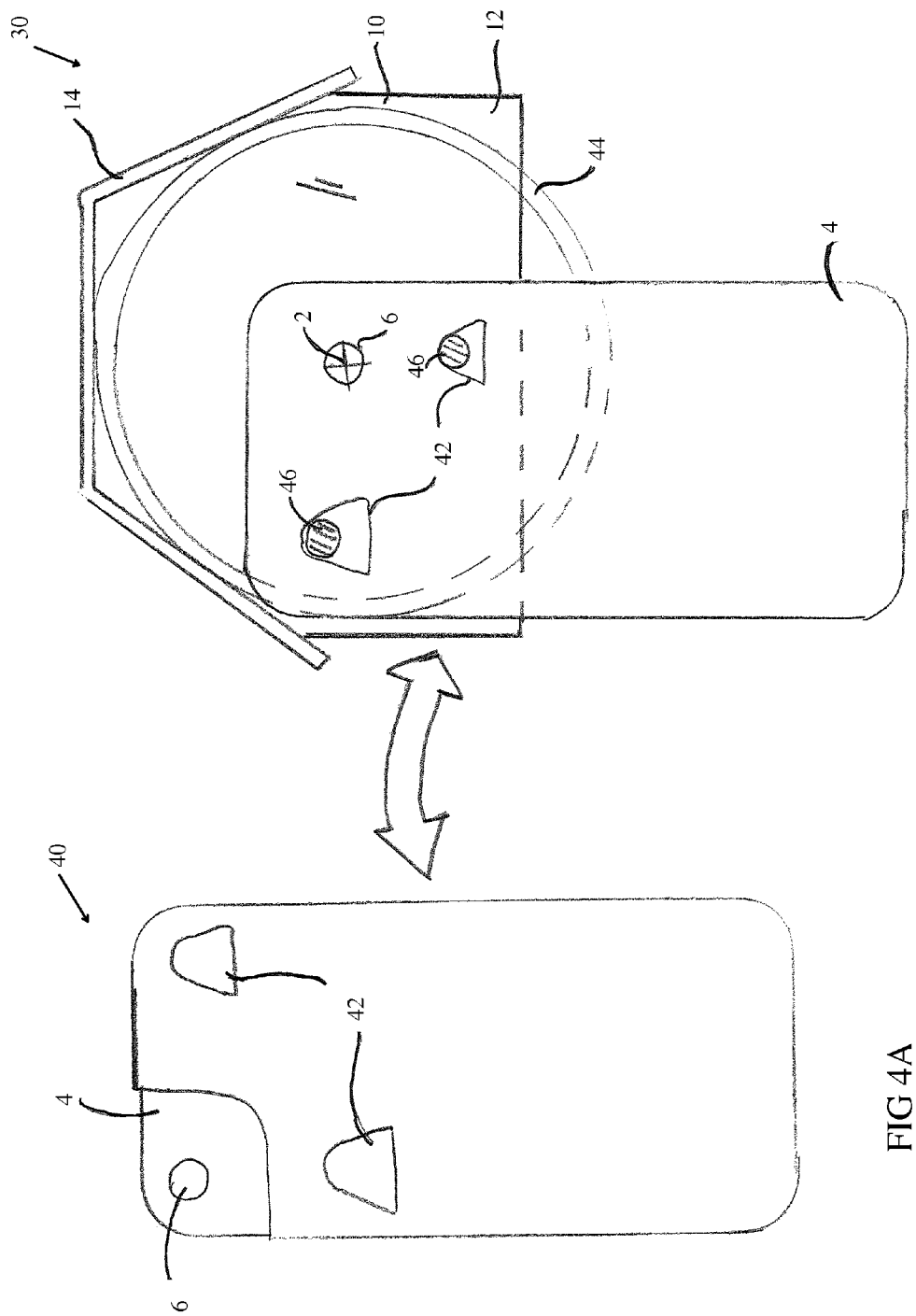

SLIT LAMP ADAPTOR FOR PORTABLE CAMERA

PRIORITY CLAIM

This application claims the benefit of U.S. Provisional Application No. 61/518,610 filed on May 9, 2011, the subject matter of which is incorporated herein by reference in its entirety.

FIELD OF THE INVENTION

This invention relates generally to an adaptor for a slit lamp for ophthalmological purposes configured to couple a portable camera to the slit lamp for photographing a patient's eye.

BACKGROUND OF THE INVENTION

Slit lamps are the main examination instrument used during an eye examination. It allows the doctor to see magnified an illuminated view of the different structures of the eye. The doctor often needs to document the visual appearance of the many different pathologic processes visualized at the slit lamp. Simple drawings can be used, but photographs are much more informative. Dedicated slit lamps for photography are available, but are expensive. Optical adaptors are available for dedicated cameras, but are also significantly expensive, and often include a beam splitter within the optical housing of the slit lamp, which can reduce the illumination. Other slit lamp models have built-in digital cameras, but these are also expensive.

The rapid evolution of technology in cell phones have brought to the market fairly advanced photographic capabilities in the cell phone handset. Many cell phones boast 5 megapixel cameras or more. The ubiquitous photographic capabilities of the cell phone yields significant potential for use in the optometric or ophthalmologic office.

SUMMARY OF THE INVENTION

The present invention is a simple, inexpensive adaptor for a slit lamp which allows a cell phone to very quickly and easily be used to capture a photographic image through the slit lamp. Features of the invention allow it to fit the many different eyepiece sizes, as well as eyepiece configurations on the various models of slit lamps. In addition, features of this adaptor allow it to accommodate various cell phone sizes and designs, as well as accommodating the multitude of cases for each cell phone model.

The present invention is directed to an adaptor for a slit lamp having an ocular. The adaptor comprises an ocular engaging portion configured to couple to an ocular of the slit lamp, a camera support configured to couple to a portable camera. The camera support is further configured to couple to the ocular engaging portion with the camera positioned relative to the ocular such that the camera can photograph a patient's eye through the ocular. The ocular engaging portion includes a transparent back plate, and the portable camera is positioned relative to the transparent back plate to photograph through the transparent back plate. The adaptor also includes a hood coupled to the transparent back plate and configured to rest upon a top surface of the ocular to maintain the ocular engaging portion in place relative to the ocular. The adaptor can also include a base plate and a flange coupled to the base plate, and a retaining arm. The base plate, flange, and retaining arm are configured to support the portable camera relative to the ocular. The base plate is configured to secure to the transparent back plate of the ocular engaging portion.

The present invention is also directed to a method of photographing a patient's eye using a portable camera and a slit lamp, including positioning an adaptor relative to the slit lamp. The adaptor comprises an ocular engagement portion configured to engage with a viewing area of the slit lamp and a camera support. The method also includes securing a portable camera to the camera support of the adaptor with the portable camera directed toward the viewing area of the slit lamp, and photographing the patient's eye with the camera through the viewing area of the slit lamp.

The present invention is also directed to an adaptor for coupling a portable camera to a slit lamp including a transparent base plate having a mounting point, and an ocular hood coupled to the base plate and being configured to engage with an ocular of the slit lamp. The adaptor also has a camera positioning unit having a support for a portable camera that is adjustably coupled to the base plate at the mounting point. The camera positioning unit is configured to position the portable camera relative to the base plate to photograph a subject through the slit lamp through the base plate.

BRIEF DESCRIPTION OF THE DRAWINGS

Preferred and alternative examples of the present invention are described in detail below with reference to the following drawings:

FIGS. 4A and 4B illustrate an adaptor and camera support according to embodiments of the present invention.

DETAILED DESCRIPTION OF THE PREFERRED EMBODIMENT

Figure 1:
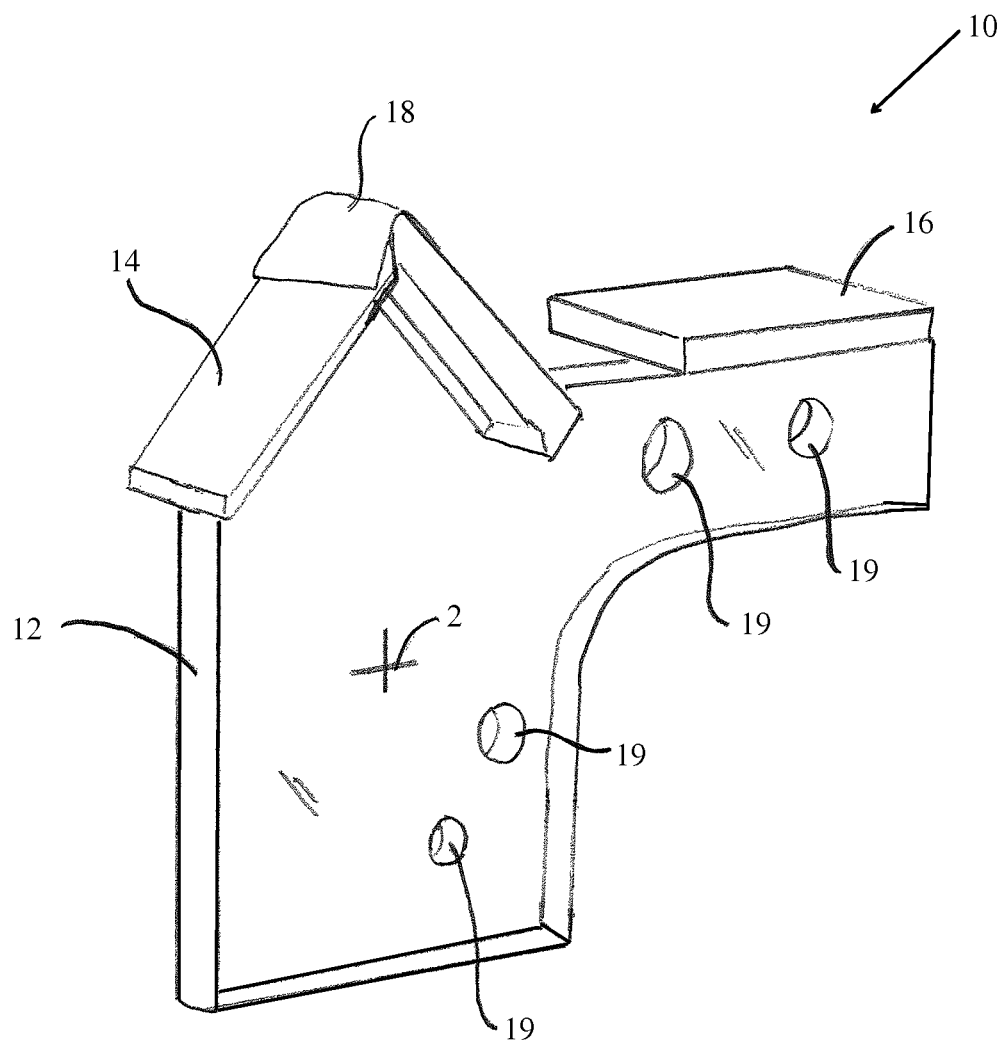
FIG. 1 illustrates an ocular engaging portion of an adaptor for use with a portable camera and a slit lamp according to embodiments of the present invention.

FIG. 1 shows an ocular engaging portion 10 of a camera adaptor according to embodiments of the present disclosure. The adaptor permits a practitioner to easily position a portable camera, such as a cell phone having a built-in camera, relative to a slit lamp to photograph a patient's eye. The present invention therefore provides inexpensive and simple slit lamp photography without expensive equipment. The ocular engaging portion 10 is designed to be placed upon an ocular of the slit lamp for use to view a patient's eye. Standard slit lamps have double oculars that are generally cylindrical, but can have other shapes as well. The present invention can also be used with other viewing equipment, such as microscopes and telescopes that may have double or single oculars. The ocular has an optical axis that extends along the viewing direction of the ocular. The ocular engaging portion 10 of the camera adaptor has a base plate 12, a hood 14, and a retaining flange 16. The base plate 12 is transparent and generally flat and is placed over the ocular with the hood 14 resting on top of the cylindrical ocular and with the base plate 12 generally perpendicular with the optical axis of the ocular. The hood 14 can include a clamp that secures to the ocular under pressure, such as with a spring or a living hinge to grasp the ocular. The base plate 12 has an alignment point 2 that is aligned with the optical axis of the ocular. The hood 14 extends over a portion of the ocular and the L-shaped structure of the hood 14 helps to center the alignment point 2 relative to the ocular. Different oculars have different diameters, so the hood 14 can be specifically designed for a particular ocular, or can have adjustability to permit the hood 14 to engage oculars of varying sizes. The retaining flange 16 can rest on another portion of the ocular or the slit lamp to prevent the camera support 10 from rotating around the ocular. The hood 14 and retaining flange 16 can have different dimensions and configurations depending on the particulars of a given ocular and slit lamp assembly. For example, the camera support 10 can have two hoods 14 for use with a slit lamp with double oculars. In some embodiments the hood 14 has an attachment member 18, such as a strip of hook-and-loop material that can engage with a strap (not shown) attached to the ocular. The base plate 12 also has a plurality of holes 19 spaced variously around the base plate. The holes 19 are used to attach to other components of the camera adaptor as described more fully below.

Figure 2:
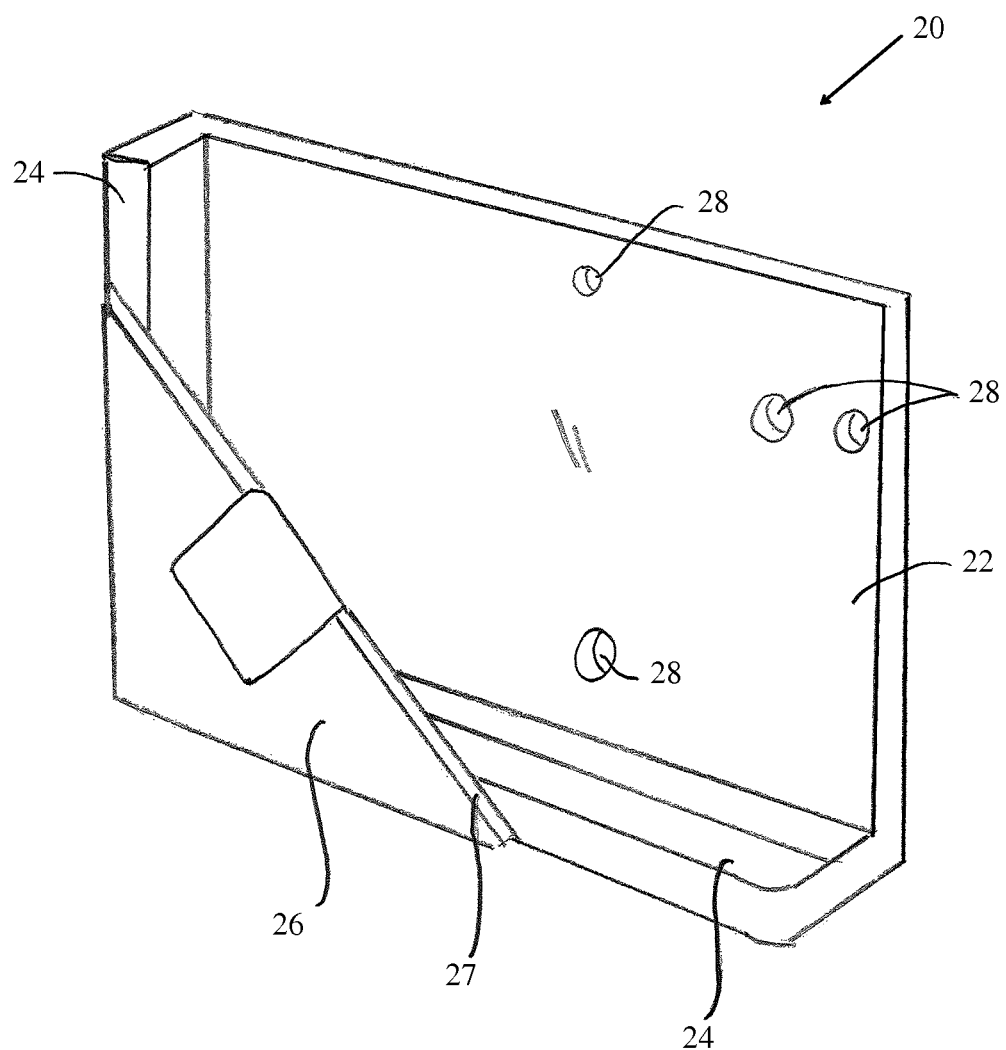
FIG. 2 illustrates a camera support according to embodiments of the present invention.

FIG. 2 illustrates a camera support 20 of the adaptor according to embodiments of the present invention. The camera support 20 has a back plate 22, a retaining flange 24, and a retaining arm 26. The back plate 22 is generally flat and can be transparent in at least some areas. The retaining flange 24 extends orthogonally from the back plate 22, and the retaining arm 26 extends orthogonally from the flange 24. The retaining arm 26 can have a diagonal edge 27 to facilitate inserting a portable camera into the camera support 20. The camera support 20 has several holes 28 similar to the holes 19 in the ocular engaging portion 10. The camera support 20 is coupled to the ocular engaging portion 10 with the base plate 12 contacting the back plate 22, and using the holes 19 and 28 to secure the pieces together. The holes 19 in the base plate 12 are larger than strictly necessary to allow the camera support 20 to be positioned relative to the ocular engaging portion 10. A portable camera, such as a cell phone having a built-in camera, can be placed into the camera support 20 with the camera aligned with the alignment point 2 on the ocular engaging portion 10. The camera is then positioned to view and photograph down the ocular to record what is visible through the ocular.

Figure 3:
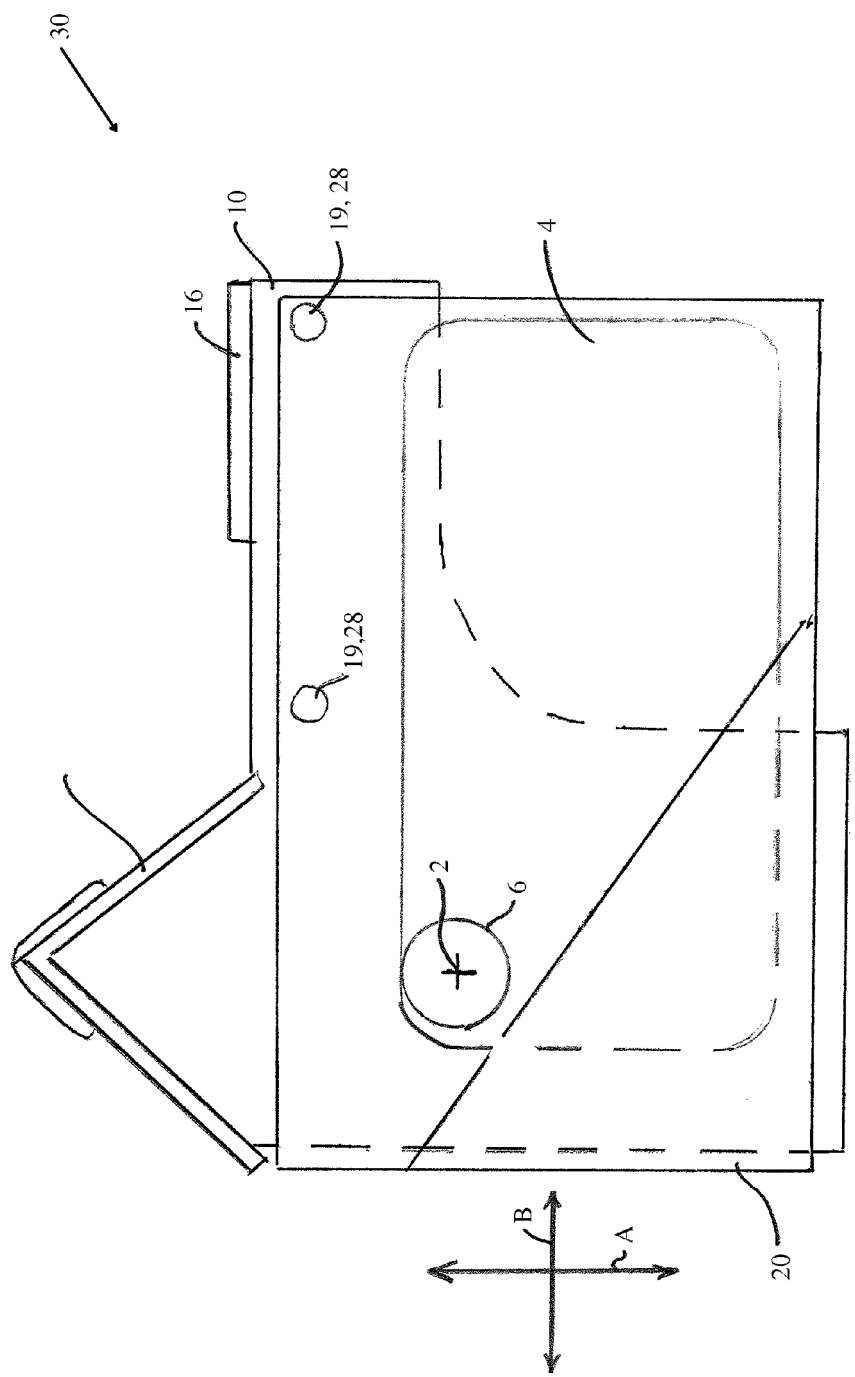
FIG. 3 is a plan view of the adaptor according to embodiments of the present invention.

FIG. 3 is a plan view of an adaptor 30 according to embodiments of the present invention including an ocular engaging portion 10 and a camera support 20 coupled together and supporting a portable camera 4. The camera 4 is resting in the camera support 20 with the aperture 6 of the camera 4 aligned with the alignment point 2 of the base plate 12. In use, a practitioner places the ocular engaging portion 10 onto the ocular, and then mounts the camera support 20 to the ocular engaging portion 20 using threaded fasteners, such as thumbscrews, or other attachment means such as clamps, clips, or snap-fit connectors. The practitioner then places the camera 4 into the camera support 20 and photographs the patient's eye, or any other suitable subject. The camera support 20 and the ocular engaging portion 10 are transparent so the camera 4 can photograph through them.

The dimensions of the adaptor 30 can be chosen according to known slit lamps and/or oculars. In some embodiments, the dimensions are chosen for a specific make or model of slit lamp and/or ocular. In other embodiments, the ocular engaging portion 10 and camera support 20 can be adjustable relative to one another to align the camera 4 with the ocular. Virtually any type of camera or cell phone can be used. The aperture 6 of the camera 4 can be moved along the optical axis of the ocular by inserting spacers between the ocular engaging portion 10 and the camera support 20, or between the camera support 20 and the camera 4 itself. The aperture 4 can be positioned in a direction orthogonal to the optical axis, such as up and down A and side to side B, by adjusting how the camera support 20 is coupled to the ocular engaging portion 10, or by positioning the camera 4 within the camera support 20.

FIGS. 4A and 4B show an adaptor 30 and a camera 4 according to embodiments of the present invention. FIG. 4A shows a camera side of the camera 4, and 4B illustrates the opposite side of the camera 4 engaged with the adaptor 30. The adaptor 30 includes a camera support 40 according to further embodiments of the present invention. The camera support 40 can be an unobtrusive case for the camera 4. The camera support 40 can be a slim, low profile covering, similar to a protective case, that protrudes from the camera 4 by no more than approximately one quarter inch. The camera support 40 can be slim enough for the practitioner to leave the camera support 40 on the camera 4 at all times. The camera support 40 includes attachment points 42 variously spaced apart, and an opening that allows the aperture 6 of the camera 4 to operate unobstructed.

FIG. 4B shows an ocular engaging portion 10 having a base plate 12 and a hood 14 for engaging an ocular 44 of a slit lamp. The base plate 12 includes pegs 46 that engage the attachment points 42 on the camera support 40 and hold the camera 4 in position with the aperture 6 aligned with the alignment point 2 and the optical axis of the ocular 44. The spacing and dimensions of the attachment points 42 and the pegs 46 can depend on the dimensions of the camera 4 and the ocular 44. In some embodiments, the camera support 40 is designed for a known, popular model of camera, such as an IPHONE™ or an ANDROID™ device. In other embodiments, the camera support 40 can be adjustable to accommodate virtually any type of camera 4.

In other embodiments, the adaptor 30 can have three parts: an ocular engaging portion, a camera support, and an intermediate member positioned between the ocular engaging portion and the camera support. The ocular engaging portion can be a small, unobtrusive component such as a peg or a post that is left mounted to the ocular and does not interfere with normal use of the slit lamp. The camera support can be similar to the unobtrusive phone case described above, such that the practitioner can leave the camera support mounted to the phone always. When the practitioner decides to photograph through the slit lamp, he simply mounts the intermediate member to the ocular engaging portion and mounts the camera support to the intermediate member. The practitioner can then very easily photograph through the slit lamp with very little set up time and at a very reduced cost.

The adaptors 30 disclosed herein therefore permit simple and easy photography of a subject through a slit lamp or another device having an ocular, such as a microscope, without requiring expensive equipment and expertise. The practitioner can quickly configure the adaptor and insert the camera into the adaptor and take digital photographs with ease. The present invention also includes a software component, such as an app for a smart phone, that can catalogue photographs taken by patient name, by location, and by date. The camera can be actuated by a voice command to free the practitioner's hands during the procedure. The camera can be virtually any type of wireless digital device capable of sending and receiving wireless transmissions such as MMS messages and email. The practitioner can therefore very easily input the patient's information into the device, insert the device into the adaptor, and photograph the patient's eye. The device can then wirelessly transmit the photographs for viewing, analysis, and diagnosis.

While the preferred embodiments of the invention has been illustrated and described, as noted above, many changes can be made without departing from the spirit and scope of the invention. By way of example, the adaptor can be made of Plexiglas, plastic, or another suitable transparent material, or the adaptor can be opaque and can include an aperture through which the camera photographs. The camera can be a digital camera, a cell phone, a smart phone, or any other type of camera. The camera support and ocular engaging portion can be coupled together using any suitable mechanical connector, including a clip, a clamp, threaded fasteners, thumbscrews, hook-and-loop fasteners, etc. The adaptor can be used with another type of device, such as a microscope or binoculars or a telescope. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. An adaptor for a slit lamp having an ocular, the adaptor comprising:
   an ocular engaging portion that comprises a hood and an alignment point that is configured to couple to the ocular of the slit lamp, wherein the hood comprises an L-shaped structure configured to rest upon a top surface of the ocular and align the alignment point with an optical axis of the ocular; and
   a camera support configured to couple to a portable camera, wherein the camera support is further configured to couple to the ocular engaging portion with the camera positioned relative to the ocular such that the camera can photograph a patient's eye through the ocular.

2. The adaptor of claim 1 wherein the portable camera comprises a cell phone camera.

3. The adaptor of claim 1 wherein the ocular engaging portion further comprises:
   a transparent back plate, wherein the portable camera is positioned relative to the transparent back plate to photograph through the transparent back plate, wherein
   the hood is coupled to the transparent back plate and configured to rest upon the top surface of the ocular to maintain the ocular engaging portion in place relative to the ocular.

4. The adaptor of claim 3 wherein the camera support comprises:
   a base plate;
   a flange coupled to the base plate; and
   a retaining arm, wherein the base plate, flange, and retaining arm are configured to support the portable camera relative to the ocular, and wherein the base plate is configured to secure to the transparent back plate of the ocular engaging portion.

5. The adaptor of claim 1 wherein the camera support comprises a case for the portable camera having a low profile that protrudes from the portable camera by less than about one quarter inch.

6. The adaptor of claim 5 wherein the ocular adaptor is configured according to known dimensions of an existing slit lamp.

7. The adaptor of claim 1, further comprising an ocular rest configured to engage the ocular and prevent the ocular engaging portion from rotating relative to the ocular.

8. The adaptor of claim 1 wherein the ocular engaging portion has protrusions and wherein the camera support has recesses configured to receive the protrusions on the ocular engaging portion.

9. The adaptor of claim 1, further comprising a strap coupled to the slit lamp and to the adaptor to further secure the adaptor to the slit lamp.

10. The adaptor of claim 9 wherein the strap comprises a fabric strip coupled to the slit lamp and the adaptor with a hook-and-loop fastener.

11. A method of photographing a patient's eye using a portable camera and a slit lamp having an ocular, the method comprising:
    positioning an adaptor relative to the slit lamp, wherein the adaptor comprises an ocular engagement portion comprising a hood and an alignment point that is configured to engage with a viewing area of the slit lamp and a camera support, wherein the hood comprises an L-shaped structure configured to rest upon a top surface of the ocular and align the alignment point with an optical axis of the ocular;
    securing a portable camera to the camera support of the adaptor with the portable camera directed toward the viewing area of the slit lamp;
    photographing the patient's eye with the camera through the viewing area of the slit lamp.

12. The method of claim 11 wherein positioning the adaptor relative to the slit lamp comprises placing the ocular engaging portion onto the ocular of the slit lamp.

13. The method of claim 11 wherein at least a portion of the adaptor is transparent, and wherein photographing the patient's eye through the viewing area comprises photographing the patient's eye through the transparent portion of the adaptor.

14. The method of claim 11 wherein the portable camera comprises a wireless digital device, the method further comprising recording a photograph of the patient's eye on the wireless digital device and transmitting the photograph from the wireless digital device.

15. The method of claim 14 wherein transmitting the photograph from the wireless digital device comprises at least one of sending an MMS message, an email message, or another digital transmission from the wireless digital device.

16. An adaptor for coupling a portable camera to a slit lamp, the adaptor comprising:
    a transparent base plate having a mounting point;
    an ocular hood coupled to the base plate and being configured to engage with an ocular of the slit lamp, wherein the ocular hood includes an L-shaped structure configured to rest upon a top surface of the ocular and align the mounting point with an optical axis of the ocular;
    a camera positioning unit having a support for a portable camera, the camera positioning unit being adjustably coupled to the base plate at the mounting point, wherein the camera positioning unit is configured to position the portable camera relative to the base plate to photograph a subject through the slit lamp through the base plate.

17. The adaptor of claim 16 wherein the portable camera comprises a cell phone.

18. The adaptor of claim 16 wherein the ocular hood comprises a clamp that resiliently engages the ocular of the slit lamp.

19. The adaptor of claim 16 wherein the optical axis of the ocular is generally aligned with the ocular, and wherein the mounting point permits the camera positioning unit to be adjusted relative to the ocular along the optical axis and along a direction orthogonal to the optical axis.

20. The adaptor of claim 19 wherein the mounting point comprises a hole in the base plate and wherein the camera positioning unit comprises a threaded fastener configured to engage the hole to adjustably mount the camera positioning unit relative to the ocular.

21. The adaptor of claim 19, further comprising a spacer positioned between either the base plate and the camera positioning unit or between the portable camera and the camera positioning unit to adjust the position of the portable camera relative to the ocular substantially along the optical axis.

* * * * *